United States Patent [19]

Schulz et al.

[11] Patent Number: 5,487,816
[45] Date of Patent: Jan. 30, 1996

[54] PROCESS FOR THE REDUCTION OF PHENOL CONTENT IN A CRUDE ORGANIC STREAM RECOVERED FROM A PHENOL STRIPPER

[75] Inventors: Russell C. Schulz, Glen Ellyn; Constante P. Tagamolila, Arlington Heights; Patrick J. Bullen, Elmhurst, all of Ill.

[73] Assignee: UOP, Des Plaines, Ill.

[21] Appl. No.: 277,686

[22] Filed: Jun. 24, 1994

[51] Int. Cl.$^6$ .............................. B01D 3/34; C07C 37/74
[52] U.S. Cl. .......................... 203/14; 203/36; 203/37; 203/98; 568/749; 568/754
[58] Field of Search .................. 203/DIG. 16, 36, 203/37, 94, 99, 98, DIG. 19; 568/749, 754, 757

[56] References Cited

U.S. PATENT DOCUMENTS

| | | | |
|---|---|---|---|
| 4,634,796 | 1/1987 | Suciu et al. | 203/34 |
| 4,851,086 | 7/1989 | Khonsari et al. | 203/45 |
| 5,064,507 | 11/1991 | O'Donnell et al. | 203/34 |
| 5,091,058 | 2/1992 | Davie | 203/33 |
| 5,122,234 | 6/1992 | Elishewitz et al. | 203/96 |
| 5,131,984 | 7/1992 | Chan et al. | 203/DIG. 19 |

FOREIGN PATENT DOCUMENTS 0039036  3/1979  Japan ........................... 203/36

Primary Examiner—Virginia Manoharan
Attorney, Agent, or Firm—Thomas K. McBride; John G. Tolomei; John G. Cutts, Jr.

[57] ABSTRACT

A process to separate in a fractionation zone an admixture comprising phenol, alpha-methylstyrene and water to produce an alpha-methylstyrene stream containing a minimum of phenol. The pH of the overhead aqueous phase is adjusted with a base to greater than about 6.

5 Claims, 1 Drawing Sheet

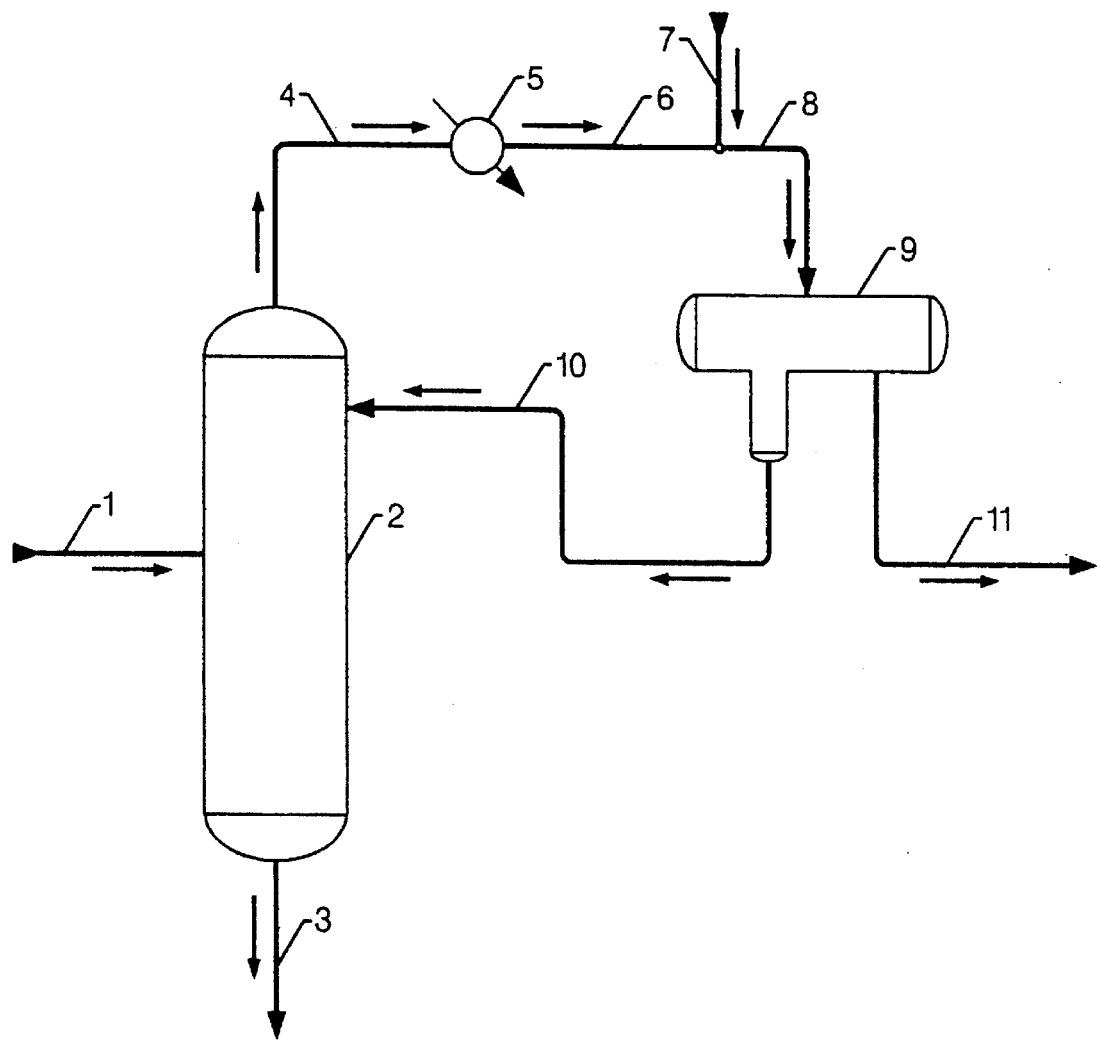

PROCESS FOR THE REDUCTION OF PHENOL CONTENT IN A CRUDE ORGANIC STREAM RECOVERED FROM A PHENOL STRIPPER

FIELD OF THE INVENTION

The field of art to which this invention pertains is the separation of an admixture of phenol and alpha-methylstyrene to produce an alpha-methylstyrene stream containing a minimum of phenol.

BACKGROUND OF THE INVENTION

During the production of phenol, not only is phenol produced but a co-product is alpha-methylstyrene which must be separated from phenol and recovered. In general, phenols are prepared by the oxidation of an alkyl-substituted aromatic hydrocarbon and the subsequent acid cleavage of the resulting alpha hydroperoxy derivative thereof to form a reaction mixture comprising a phenol, a ketone and an unreacted alkyl-substituted aromatic hydrocarbon. The acid cleavage is generally effected in the presence of an aqueous acid catalyst, usually 50–98% sulfuric acid in aqueous solution, and preferably at least 70%, or in the presence of an aqueous hydrochloric or perchloric acid solution. The recovery process of the present invention is particularly suited for use in conjunction with a process wherein phenol is prepared by the air oxidation of cumene and the subsequent sulfuric acid cleavage of the resulting cumene hydroperoxide to form a reaction mixture comprising phenol, acetone and unreacted cumene. In addition to the principal products, varying amounts of by-products are formed such as mesityl oxide, alpha-methylstyrene, methyl-benzofuran, p-cumylphenol, phenyldimethylcarbinol, acetophenone and higher molecular weight phenolics.

In the initial stage of recovering phenol from the acid cleavage reaction mixture, the acidic reaction mixture is initially neutralized, either directly by the addition of caustic followed by the separation of the organic phase from the aqueous phase which contains the sodium salt of the acid catalyst, or indirectly by contact with an ion exchange resin. In any case, the resulting neutralized reaction mixture is fed to a distillation column, commonly referred to as a crude acetone column, at conditions to effect a crude separation of those materials boiling below phenol whereby an overhead fraction is recovered comprising substantially all of the acetone and lower boiling by-products, as well as a substantial portion of the water and unreacted cumene. Acetone is subsequently recovered, as is cumene, by the further distillation of the crude acetone column overhead, the cumene being recycled to the oxidation step.

The bottoms fraction recovered from the crude acetone column, containing phenol, alpha-methylstyrene and heavy by-products as well as the balance of the water and unreacted cumene, is typically treated for the separation of heavy by-products and thereafter fed to a distillation column, commonly referred to as a cumene or alpha-methylstyrene column. The last-mentioned column is operated at conditions to separate an overhead fraction comprising water and cumene from the higher boiling phenol product. The phenol, recovered as the bottoms fraction, further contains impurities such as acetophenone, mesityl oxide, methyl benzofuran, hydroxy acetone, alpha-methylstyrene and a small amount of residual cumene for example. The phenol is introduced into a phenol stripper column with water to fractionate the lower boiling components consisting mainly of alpha-methylstyrene and to strip out the hard-to-fractionate trace amounts of contaminates such as methyl benzofuran and mesityl oxide; and to produce a bottoms stream containing phenol and heavier boiling components which may be further processed as required. The overhead stream from the phenol stripper column contains water, phenol, methyl benzofuran, alpha-methylstyrene and lower boiling organic components. A condensed aqueous stream containing phenol is refluxed to the phenol stripper column and a condensed net organic phase containing alpha-methylstyrene is recovered. Because of the formation of a phenol-water azeotrope, a significant amount of phenol leaves with the stripper overhead vapor which is largely comprised of water vapor and the alpha-methylstyrene and the lower boiling hydrocarbons. The resulting condensed organic phase containing mainly alpha-methylstyrene is scrubbed with caustic to remove phenol. The spent caustic from the scrubbing operation is subsequently treated with sulfuric acid in order to recover the phenol for recycle to the process. High phenol content in the mainly alpha-methylstyrene phase translates to increased consumption of caustic and sulfuric add, and burdens the associated equipment.

INFORMATION DISCLOSURE

U.S. Pat. No. 5,064,507 discloses a process for producing high purity phenol wherein a crude phenol product stream containing alpha-methylstyrene (AMS), acetol, 2-phenylpropionaldehyde (2 PPA), methyl-benzofuran (MBF), mesityl oxide (MO) and carbonyl impurities is treated in a first treatment zone with an amine to convert acetol and 2 PPA to higher boiling components; the treated stream is distilled to separate higher boiling components and to produce an overhead stream containing phenol, AMS and impurities including MBF, MO and carbonyl compounds; the overhead stream is steam distilled with water to recover a light product containing phenol, water, AMS, MBF and carbonyl compounds and a heavy product containing phenol having a reduced quantity of MBF, AMS and carbonyl compounds; and the steam distillation includes a second amine treatment step whereby an effective amount of a low volatility amine is added to the lower portion of the distillation column to convert MO and carbonyl impurities to heavy and light impurities to enable the recovery of high purity phenol.

The low volatility amine is introduced into the steam distillation column to achieve the conversion of MO and carbonyl impurities into compounds which are readily separated in the steam distillation column. Commercially, in the event that a lower grade of phenol is produced, such as resin grade phenol, for example, the expensive amine injection is discontinued for the sake of economy.

BRIEF SUMMARY OF THE INVENTION

The present invention provides a process for the separation of an admixture of phenol, alpha-methylstyrene and lower boiling organic components and water to produce an organic stream containing a minimum of phenol. It has unexpectedly been discovered that if during the fractionation of phenol, alpha-methylstyrene and lower boiling organic components, the condensed overhead stream is maintained at a pH greater than about 6, a larger portion of the phenol partitions to the aqueous phase. This preferred partition of the phenol produces an organic phase containing a minimum concentration of phenol. The pH control is preferably performed by the introduction of ammonia or ammonium hydroxide into the overhead system of the fractionator. The process of the present invention enjoys the advantage of using less quantities of caustic and sulfuric acid during the purification of the resulting organic stream containing mainly alpha-methylstyrene and the recovery of phenol from the spent caustic. In addition, the presence of a higher pH in the fractionator will decrease the corrosion of the metal surfaces of the fractionating vessel and its internals and the piping that carries the net aqueous and product overhead streams.

One embodiment of the present invention may be characterized as a process for the separation of an admixture comprising phenol, alpha-methylstyrene (AMS) and water to produce an organic stream comprising alpha-methylstyrene and phenol which process comprises: (a) introducing the admixture comprising phenol, alpha-methylstyrene and water into a fractionation zone; (b) removing a high purity stream of phenol from the bottom of the fractionation zone; (c) removing an overhead vapor stream comprising alpha-methylstyrene, phenol and water from the fractionation zone; (d) condensing at least a portion of the overhead vapor stream to produce an aqueous stream comprising phenol and an organic phase comprising alpha-methylstyrene and phenol; (e) introducing a base to maintain the pH of the aqueous stream comprising phenol greater than about 6; (f) refluxing at least a portion of the aqueous stream comprising phenol and having a pH greater than about 6 to the fractionation zone; and (g) recovering an organic stream comprising alpha-methylstyrene and phenol.

Another embodiment of the present invention may be characterized as a process for the separation of an admixture comprising phenol, alpha-methylstyrene (AMS) and water to produce an organic stream comprising alpha-methylstyrene and phenol which process comprises: (a) introducing the admixture comprising phenol, alpha-methylstyrene and water into a fractionation zone; (b) removing a high purity stream of phenol from the bottom of the fractionation zone; (c) removing an overhead vapor stream comprising alpha-methylstyrene, phenol and water from said fractionation zone; (d) condensing at least a portion of the overhead vapor stream to produce an aqueous stream comprising phenol and an organic phase comprising alpha-methylstyrene and phenol; (e) contacting the aqueous stream comprising phenol from step (d) with a base to maintain the pH of the aqueous stream comprising phenol greater than about 6; (f) refluxing at least a portion of the aqueous stream comprising phenol and having a pH greater than about 6 to the fractionation zone; and (g) recovering an organic stream comprising alpha-methylstyrene and phenol.

BRIEF DESCRIPTION OF THE DRAWING

The drawing is a simplified flow diagram of a preferred embodiment of the present invention.

DETAILED DESCRIPTION OF THE INVENTION

The present invention provides an improved process to reduce the concentration of phenol in a stream containing alpha-methylstyrene resulting from the overhead of a fractionation column. In one embodiment of the present invention, a fractionation column, commonly referred to as a phenol stripper, is used to remove alpha-methylstyrene from a stream containing phenol and alpha-methylstyrene resulting from the previous production of phenol. The preferred feedstock for use in a phenol stripper in accordance with the present invention is an admixture containing phenol, alpha-methylstyrene and water derived from the oxidation of an alkyl-substituted aromatic hydrocarbon as described hereinabove.

The feedstock is introduced into a fractionation zone which is commonly used by prior art processes and operated at conditions which may be readily determined and selected by a person skilled in the art. In accordance with the present invention, the condensed overhead stream is maintained at a pH greater than about 6 by the addition of a base into the overhead of the fractionation zone. The resulting organic stream which is condensed from the fractionation zone overhead contains a lower portion of phenol and the aqueous phase in the overhead receiver contains a greater portion of the phenol which is removed from the top of the fractionation zone. Preferred bases are ammonia or ammonium hydroxide. In a more preferred embodiment of the present invention, the condensed overhead stream is maintained at a pH greater than about 10.

DETAILED DESCRIPTION OF THE DRAWING

In the drawing, the process of the present invention is illustrated by means of a simplified flow diagram in which such details as pumps, instrumentation, heat exchange and heat-recovery circuits, pumps and similar hardware have been deleted as being non-essential to an understanding of the techniques involved. The use of such miscellaneous equipment is well within the purview of one skilled in the art.

With reference now to the drawing, a feedstock containing phenol, alpha-methylstyrene and water resulting from the production of phenol in an air oxidation process is introduced via conduit 1 into fractionation zone 2. A high purity stream of phenol is removed from fractionation zone 2 via conduit 3 and recovered. An overhead stream containing phenol, alpha-methylstyrene and water is removed from the overhead of fractionation zone 2 via conduit 4 and is introduced into heat-exchanger 5. After the flowing stream is cooled in heat-exchanger 5, the resulting condensate is transported via conduit 6 and is contacted with a basic compound which is introduced via conduit 7 and the resulting admixture having an adjusted pH is transported via conduit 8 and is introduced into overhead receiver 9. An aqueous stream containing phenol is removed from overhead receiver 9 via conduit 10 and is introduced as reflux into fractionation zone 2. A stream of alpha-methylstyrene containing a minimum amount of phenol is removed from overhead receiver 9 via conduit 11 and recovered.

EXAMPLE

A phenol stripper column was sampled to provide an overhead aqueous phase sample and an overhead organic phase sample. The aqueous phase was found to have a pH of 8.4 and contained 5.1 weight percent phenol. The organic phase was found to contain 25.7 weight percent phenol.

The pH of four aliquots of the combined overhead aqueous phase and overhead organic phase was adjusted to give a pH of 5.0, 7.6, 9.8 and 11.0. Each pH adjusted aliquot was allowed to settle and the resulting aqueous phase and organic phase were analyzed to determine the content of phenol in each phase. A phenol separation coefficient defined as the ratio of the weight percent phenol in the organic phase to the weight percent phenol in the water phase was calculated for each corresponding pH. The results are presented in Table 1.

TABLE 1

| pH | Separation Coefficient |
|---|---|
| 5.0 | 6.0 |
| 7.6 | 5.2 |
| 8.4 | 5.0 |
| 9.8 | 2.6 |
| 11.0 | 1.8 |

From the results presented in Table 1, it is seen that as the pH is increased, the separation coefficient decreases which represents that the phenol content in the organic phase containing alpha-methylstyrene is reduced.

The foregoing description, drawing and example clearly illustrate the advantages encompassed by the process of the present invention and the benefits to be afforded with the use thereof.

What is claimed:

1. A process for the separation of an admixture comprising phenol, alpha-methylstyrene (AMS) and water to produce an organic stream comprising alpha-methylstyrene and phenol which process comprises:

(a) introducing said admixture comprising phenol, alpha-methylstyrene and water into a fractionation zone;

(b) removing a high purity stream of phenol from the bottom of said fractionation zone;

(c) removing an overhead vapor stream comprising alpha-methylstyrene, phenol and water from said fractionation zone;

(d) condensing at least a portion of said overhead vapor stream to produce an aqueous phase comprising phenol and an organic phase comprising alpha-methylstyrene and phenol;

(e) introducing a base into the overhead of said fractionation zone to maintain the pH of said aqueous phase comprising phenol greater than about 6 so as to partition a large portion of the phenol into the aqueous phase from the organic phase;

(f) refluxing at least a portion of said aqueous phase comprising phenol and having a pH greater than about 6 to said fractionation zone; and (g) recovering an organic stream comprising alpha-methylstyrene and phenol.

2. The process of claim 1 wherein said high purity stream of phenol from step (b) comprises at least about 99 weight percent phenol.

3. The process of claim 1 wherein said base is selected from the group of ammonia and aqueous ammonium hydroxide.

4. The process of claim 1 wherein the pH of said aqueous phase comprising phenol is adjusted to be greater than about 10.

5. A process for the separation of an admixture comprising phenol, alpha-methylstyrene (AMS) and water to produce an organic stream comprising alpha-methylstyrene and phenol which process comprises:

(a) introducing said admixture comprising phenol, alpha-methylstyrene and water into a fractionation zone;

(b) removing a high purity stream of phenol from the bottom of said fractionation zone;

(c) removing an overhead vapor stream comprising alpha-methylstyrene, phenol and water from said fractionation zone;

(d) condensing at least a portion of said overhead vapor stream to produce an aqueous phase comprising phenol and an organic phase comprising alpha-methylstyrene and phenol;

(e) contacting said aqueous phase comprising phenol from step (d) with a base to maintain the pH of said aqueous phase comprising phenol greater than about 6 so as to partition a large portion of the phenol into the aqueous phase from the organic phase;

(f) refluxing at least a portion of said aqueous phase comprising phenol and having a pH greater than about 6 to said fractionation zone; and (g) recovering an organic stream comprising alpha-methylstyrene and phenol.

* * * * *